(12) United States Patent
De Godzinsky

(10) Patent No.: US 7,503,692 B2
(45) Date of Patent: Mar. 17, 2009

(54) ARRANGEMENT IN CONNECTION WITH INTRA-ORAL X-RAY IMAGING

(75) Inventor: Christian De Godzinsky, Vanda (FI)

(73) Assignee: Planmeca Oy, Helsinki (FI)

( * ) Notice: Subject to any disclaimer, the term of this patent is extended or adjusted under 35 U.S.C. 154(b) by 113 days.

(21) Appl. No.: 11/572,459

(22) PCT Filed: Jul. 22, 2005

(86) PCT No.: PCT/FI2005/000336

§ 371 (c)(1),
(2), (4) Date: Jan. 22, 2007

(87) PCT Pub. No.: WO2006/008338

PCT Pub. Date: Jan. 26, 2006

(65) Prior Publication Data

US 2008/0002808 A1    Jan. 3, 2008

(30) Foreign Application Priority Data

Jul. 22, 2004    (FI) .................................. 20041010

(51) Int. Cl.
A61B 6/08    (2006.01)

(52) U.S. Cl. ........................................ 378/205; 378/38

(58) Field of Classification Search ............. 378/38–40, 378/98.8, 167, 168, 170, 204, 205
See application file for complete search history.

(56) References Cited

U.S. PATENT DOCUMENTS

| | | | | |
|---|---|---|---|---|
| 4,223,228 A | | 9/1980 | Kaplan ........................ | 378/205 |
| 4,507,798 A | | 3/1985 | Welander .................... | 378/170 |
| 4,554,676 A | | 11/1985 | Maldonado et al. ......... | 378/170 |
| 5,113,424 A | | 5/1992 | Burdea et al. ............... | 378/170 |
| 5,463,669 A | * | 10/1995 | Kaplan ........................ | 378/205 |
| 5,514,873 A | | 5/1996 | Schulze-Ganzlin et al. . | 250/394 |
| 5,632,779 A | | 5/1997 | Davidson .................... | 623/1.51 |
| 5,828,722 A | | 10/1998 | Ploetz et al. ................. | 378/38 |
| 6,343,875 B1 | | 2/2002 | Eppinger et al. ............ | 378/170 |

FOREIGN PATENT DOCUMENTS

EP    1181891 A2    2/2002
WO    WO 2004/019783 A1    3/2004

* cited by examiner

Primary Examiner—Courtney Thomas
(74) Attorney, Agent, or Firm—WolfBlock LLP

(57) ABSTRACT

This invention relates to mutual positioning of an x-ray beam and an intra-oral x-ray sensor in connection with an imaging process by utilizing at least one measurement signal, which is achieved by arranging means for producing a magnetic field resp. for measuring the magnetic field in connection with a radiation source resp. the sensor.

15 Claims, 3 Drawing Sheets

ARRANGEMENT IN CONNECTION WITH INTRA-ORAL X-RAY IMAGING

TECHNICAL FIELD

The present invention relates to positioning of an X-ray beam and an intra-oral X-ray sensor with respect to each other in connection with a dental imaging event.

BACKGROUND OF THE INVENTION

Dental intra-oral X-ray images are taken by using an X-ray examination apparatus which typically include a multi-jointed arm construction and an X-ray source placed inside a housing. Typically, an elongated collimator limiting the X-ray beam has been attached or arranged to be attached to the housing. The imaging process includes placing the X-ray device in the proximity of the object area to be imaged and aiming the X-ray beam so that it will meet the sensor in a correct orientation and at a desired angle. Typically, the X-ray beam is arranged perpendicularly with respect to a film, or some other sensor placed inside the patient's mouth.

Dental professionals do generally recognize the problems which relate to aiming and orienting the X-ray beam concentrically as well as so that, for eliminating geometric distortions and unsharpness of the image, the X-ray beam is not inclined or turned with respect to the means for receiving image data. Thus, different aiming arrangements have been developed to facilitate correct positioning of the X-ray source with respect to the sensor. One approach according to prior art is to attach the X-ray source and the means for receiving image data such as a film, a phosphorous imaging plate, a CCD sensor or other digital sensor physically to each other for the duration of irradiation.

The junction assemblies designed for physical connection of imaging means typically include an aiming arm, which may be attached both to a sensor holder/bite block and to the housing of the X-ray source. The latter connection is typically made by means of an aiming ring attached to a collimator tube of the X-ray device housing. Since there are several imaging modes in intra-oral imaging, such as the left- and right-side anterior, posterior, endodontic and bitewing imaging, assemblies comprising components of special shapes are required for supporting these special imaging modes for enabling different sensor positions and aimings of the sensor with respect to the X-ray beam. Some prior-art systems and assemblies utilising this approach are presented in patent specifications U.S. Pat. Nos. 6,343,875 B1, 5,632,779 A, 4,507,798 A and 4,554,676 A.

However, many of the dental professionals find these systems, in which the sensor placed inside the mouth should be physically connected to the X-ray device, difficult to use in practice. A reason for this is, first, that if all connections of the assembly are made prior to positioning the sensor in the mouth, it has proven difficult to direct the entire relatively heavy construction, including an X-ray tube and its arm construction, to its proper and precisely correct position. Second, if the sensor is first placed in the correct position in the mouth, assembling the construction has proven difficult—that is, e.g. connecting the aiming arm to the X-ray device so that the connecting process would not cause movement of the sensor or discomfort to the patient.

Because of these practical problems related to the above-mentioned operations, the technical advantages of these systems are frequently ignored and aiming is done by simply visually estimating the correct place and orientation of the X-ray device, possibly by using as a help the position and orientation of the aiming arm protruding from patient's mouth. One has also tried to utilise the thin aiming arm to facilitate aiming by connecting it manually e.g. to the outer surface of the collimator of the X-ray tube, with limited success, however. This is not the least because of the fact that it has proven quite difficult to keep the sensor in a correct position by keeping the thin aiming arm between one's fingers and, at the same time, direct the arm construction of the X-ray source, especially into contact with the thin aiming arm. The probability for a repeated success in achieving the same distance between the X-ray source and the image forming plane, not to mention the proper and precise orientation of the X-ray beam, is clearly not extremely high by these methods.

A further problem of prior-art aiming assemblies is that, because of the great number of different components required for supporting different intra oral imaging modes, a lot of experience or learning by trial-and-error is required in order to be able to assemble the jigsaw puzzle according to each imaging mode.

SUMMARY OF THE INVENTION

The object of the invention is to offer a novel intra-oral X-ray imaging arrangement and a method for positioning an X-ray source and a sensor with respect to each other in connection with intra-oral X-ray imaging, by means of which it may be possible to even totally avoid the need to use an aiming arm attachable to the sensor, or a corresponding device for bringing the sensor and the X-ray tube to a desired mutual position. This and other objects and advantages of the invention with respect to prior art will become apparent in the description to follow and are achievable by solutions presented in the accompanying patent claims.

The preferable embodiments of the present invention are presented by means of example in the accompanying drawings, which may be considered to be adequate for describing the invention in full. The purpose of the exemplary embodiments in question is not to show all the possible different forms and modifications by which the invention may be implemented, but the characteristics of the invention are defined in the patent claims to follow.

SHORT DESCRIPTION OF THE DRAWINGS

DETAILED DESCRIPTION OF THE INVENTION

Figure 1:
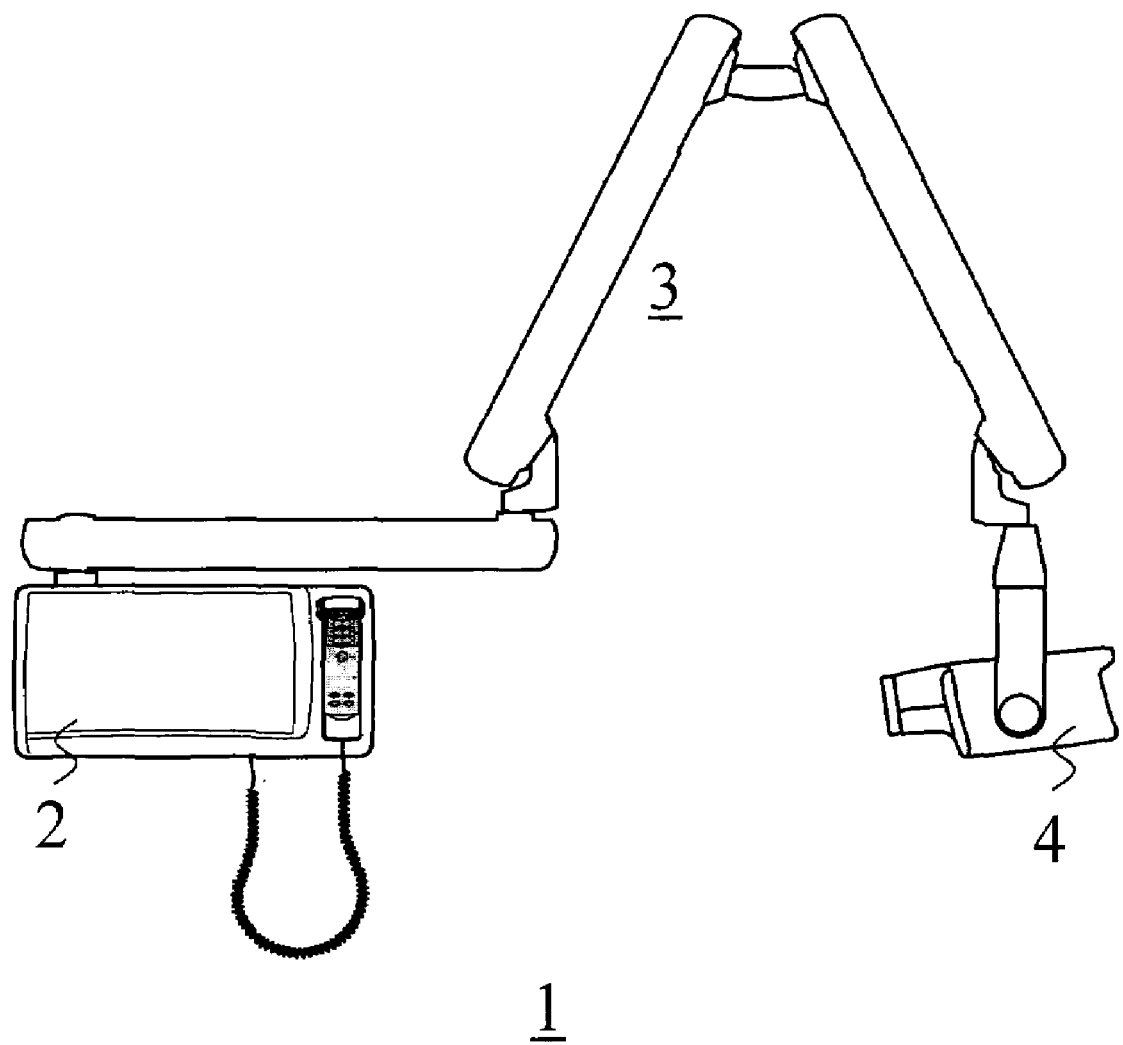
FIGS. 1, 2a and 2b show a typical intra-oral X-ray device.
Figure 2:
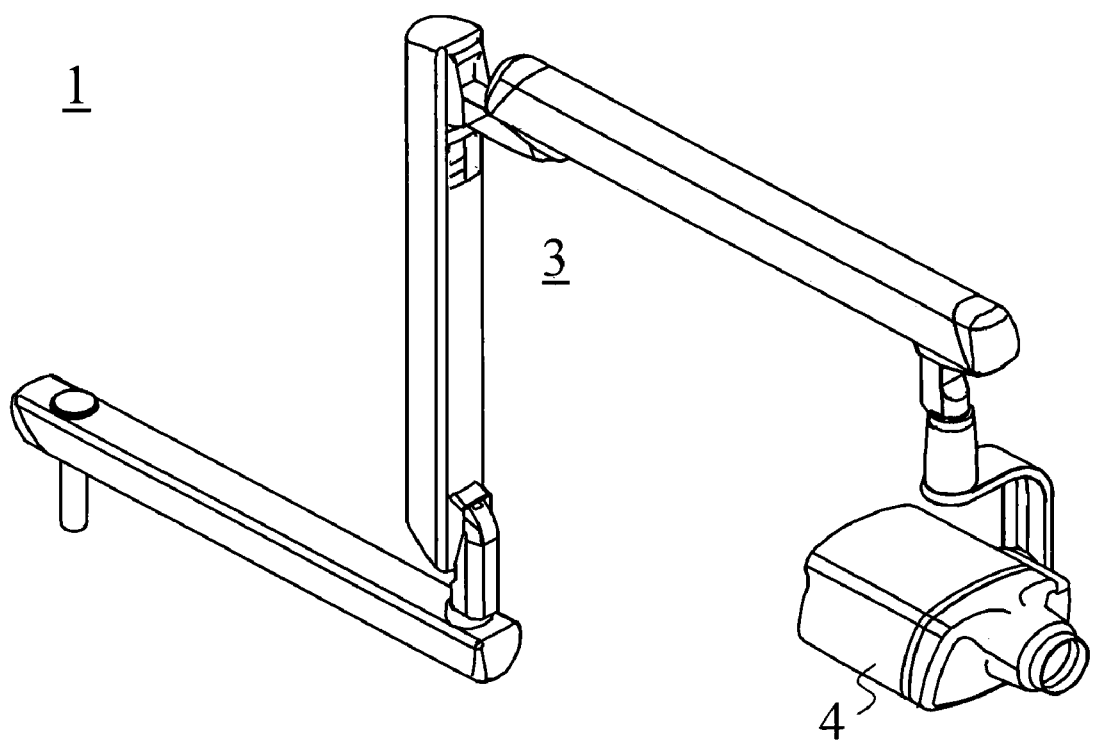
Figure 2:
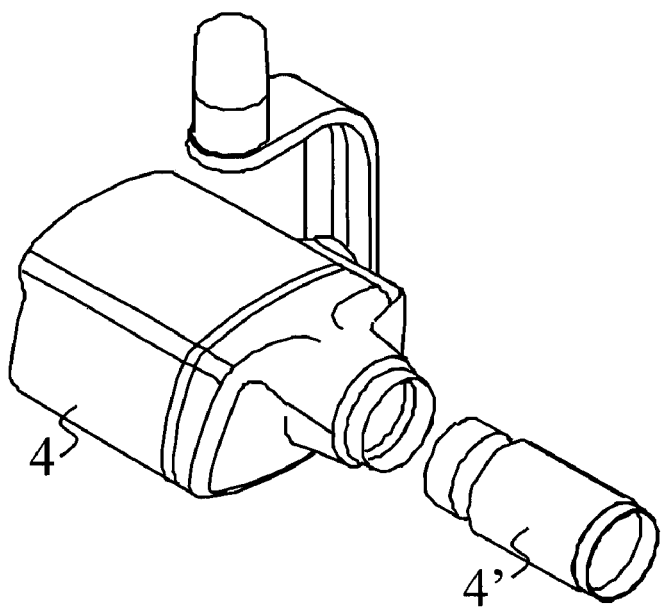

FIGS. 1, 2a and 2b show a typical intra-oral X-ray device (1) which includes a control panel (2), a jointed arm construction (3) and an X-ray source (4). FIG. 2b shows additionally an elongated collimator (4') which may be attached to the housing of the X-ray source (4) for limiting of the X-ray beam more precisely and thus minimising the radiation dose received by the patient. The multi-element arm-joint constructions (3) of intra-oral X-ray devices create a lot of degrees of freedom for positioning the X-ray source (4) in a desired manner.

Figure 3:
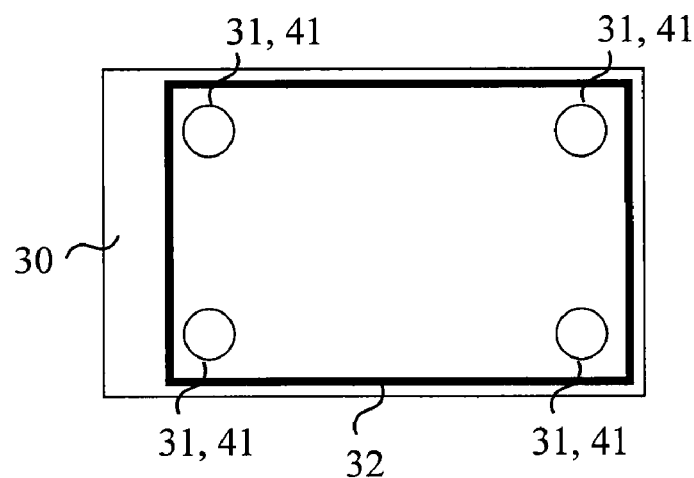
FIG. 3 shows a sensor arrangement usable in the imaging arrangement according to the invention.

FIG. 3 describes one sensor arrangement usable in the imaging arrangement according to the invention. Therein, MRI (magnetic resonance imaging) detectors (31), which measure the strength of a magnetic field, are arranged to the intra-oral sensor (30), to the corners of an area forming a rectangle which essentially does not resemble a line. When, correspondingly, a permanent magnet, or e.g. according to one preferable embodiment of the invention, an inductive transmitter is arranged to the X-ray source (4) or to its essential proximity, signals corresponding the strengths of the magnetic field measured by the MRI detectors (31) are received from them, which signals depend on the position and orientation of the sensor (30) in the magnetic field, such as the distance and the angle of inclination of the detectors (31) with respect to the inductive transmitter or the permanent magnet. Instead of MRI detectors (31), it is also possible to use small coils (41) and connect to them a means for measuring the signal received from each coil (41), the strength of which signal thus being dependent on the strength of the magnetic field in the position the coil (41) is located at a given time.

Typically, the distance of the sensor (30) and the radiation source (4) with respect to each other is desired to be able to be set the same, repeatedly, and the sensor (30) essentially perpendicularly with respect to the X-ray beam produced by the radiation source (4), and into the middle of it. Typically one tries to collimate (limit) the X-ray beam to correspond to the form and size of the sensor (30) used. The positioning or the reproductionability of positioning of the sensor (30) and the radiation source (4) with respect to each other may be facilitated already by a single signal received from one MRI detector (31) or coil (42) arranged in connection with the sensor (30), especially if the mutual distance between the sensor (30) and the radiation source (4) may be standardised by some other means. For more complete information, signals received from at least three, preferably four different coils (41) or detectors (31) are required. In the case of four coils (41) or detectors (31), they may be preferably arranged e.g. to the corners of an area forming a rectangle which essentially does not resemble a line, and three e.g. to the corners of an area forming essentially an equilateral triangle. At least one of the detectors (31) or coils (41) may also be arranged to a different plane or angle with respect to one of their mounting surfaces, with respect to at least one other detector (31) or coil (41), e.g. so that they are arranged perpendicularly with respect to one focus point.

Signals including measured values representing strengths of the magnetic fields may be sent e.g. to a display device pertaining to the user interface of the control system of the imaging arrangement or some other display device, from which one is able to monitor changing of the values in question when changing the mutual position of the sensor (30) and the X-ray source (4), and deduce from it when the positioning is as desired. The arrangement may also include a computer program, e.g. for converting the measured values in question to visually presenting the position of the sensor (30) and the X-ray source (4) with respect to each other on the screen, or some other computer program by means of which one is able to show signal data in a form which facilitates the positioning.

Figure 4:
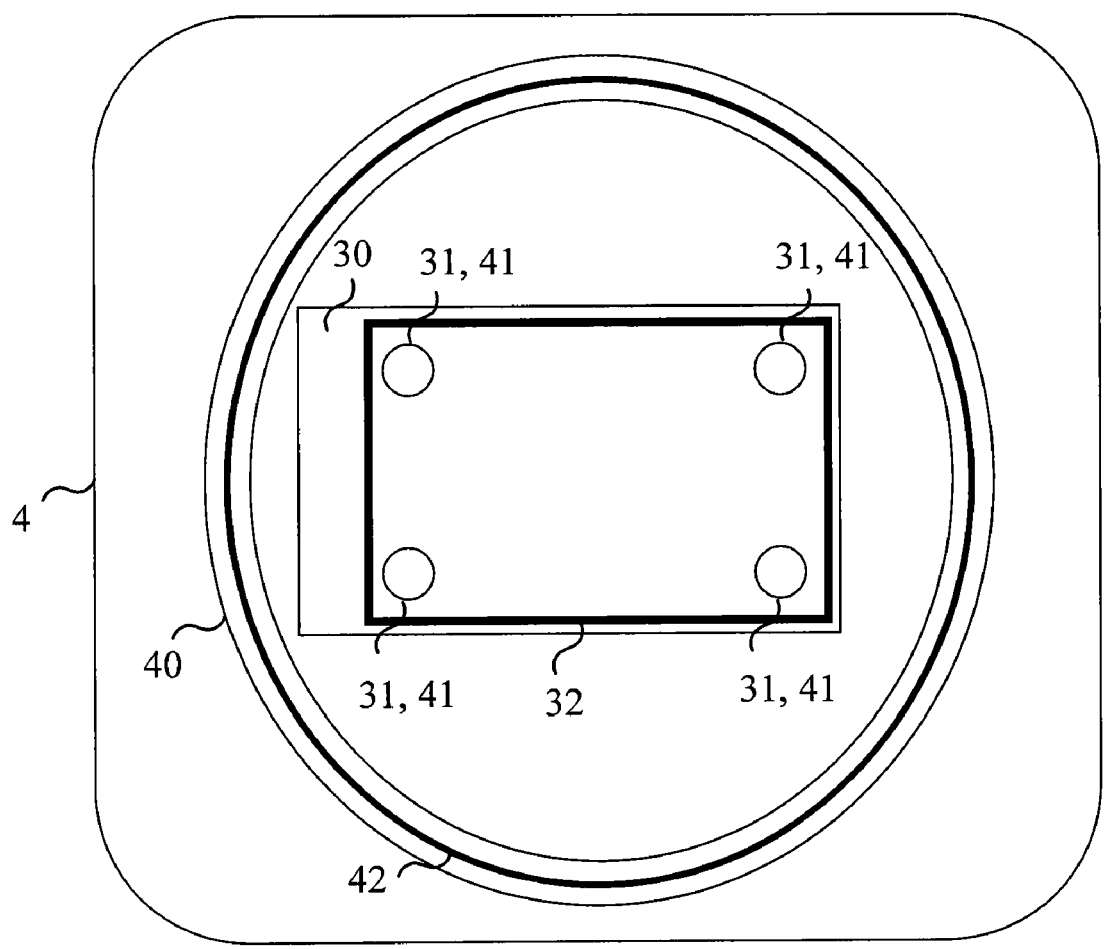
FIG. 4 shows a typical appropriate position of the sensor with respect to the position of the radiation source with respect to the X-ray beam in connection with intra-oral X-ray imaging.

As partly already referred to above, one preferable embodiment of the invention comprises a solution which utilises an inductive transmitter arranged to the radiation source (4) for other purposes, i.e., for transmitting energy. Such an inductive transmitter, or a coil (42) pertaining therein, may be attached or integrated e.g. to an adapter (40) of e.g. ring-like or rectangular shape, to be attached to the collimator (4') of the X-ray source (4). FIG. 4 shows such an adapter (40) and a coil (42) of an inductive transmitter integrated therein, as positioned with respect to the sensor (30) according to FIG. 3 in such a manner one typically tries to position it in connection with intra-oral imaging. The adapter (40) may be arranged to be attached to the end of e.g. an X-ray tube (4), or a collimator tube (4') used therein, or as integrated therewith.

Partly because of this embodiment of the invention, also the coil (32) of the inductive receiver is shown in the sensor (30) according to FIGS. 3 and 4, which coil may thus be used not only in accordance with one preferable embodiment of the invention to form an energy transmission link e.g. with an inductive transmitter arranged to the X-ray source (4) or its essential proximity, but also in a corresponding manner than described above in connection with corner coils (41), as a signal source to provide data on position of the sensor (30) in the magnetic field produced by the inductive transmitter. The coil (32) of the inductive receiver may be arranged as e.g. according to FIGS. 3 and 4 in the form of a rectangle so that it essentially imitates the form of the sensor (30) perimeter and is located in essential proximity to at least part of the sensor (30) edges. Such a coil (32) is preferable to arrange in connection with the sensor housing so that the winding will not limit the active detector surface available in the sensor (30).

One preferable embodiment of the invention thus comprises an arrangement in which an inductive transmitter is placed in the X-ray source (4), and in which small receiver coils (41) or MRI detectors (31) are arranged e.g. essentially to the corners of a sensor (4) essentially of rectangular shape, or to at least one of them. When the sensor (30) is being positioned with respect to the radiation source (4)—or in connection with intra-oral imaging, more frequently perhaps vice versa, when the X-ray source (4) is being positioned with respect to the sensor (30)—the signals received from the detectors (31) or the coils (41) change according to how their position changes in the magnetic field produced by the inductive transmitter attached to the X-ray source (4). Also the coil (32) of the inductive receiver may be arranged to be used for this purpose as well. These signals may be arranged to be sent e.g. via a wireless link (not shown in FIGS. 3 and 4) such as an RF link, as signals indicating the mutual position of the sensor (30) and the X-ray source (4), which signals may be utilised for achieving a desired mutual position of the sensor (30) and the radiation source (4).

The invention is described above mainly so that the magnetic field is produced in connection with the radiation source (4), and its strength is measured by a means arranged in connection with the sensor (30). The arrangement may also be realised in such a way that measuring of the magnetic field is arranged to be made in connection with the radiation source (4), i.e., so that the MRI detectors (31) or coils (41, 32) are arranged in connection with it, whereby the magnetic field may be produced e.g. in a permanent magnet arranged in connection with the sensor (30).

It is self evident for a man skilled in the art that the present invention may be implemented also in accordance with other embodiments than the ones presented above within the scope of protection defined by the accompanying patent claims.

The invention claimed is:

1. An intra-oral X-ray imaging arrangement, comprising (i) a radiation source (4) for producing an X-ray beam used in imaging and for aiming it to the object to be imagined (ii) a sensor (30) for detecting corresponding image data, (iii) a control system of the imaging arrangement, (iv) a means for producing a magnetic field, which means has been arranged in connection with the radiation source (4), (v) a means for measuring the strength of the magnetic field, which means has been arranged in connection with the sensor, and (vi) a means for transmitting signals including values representing strengths of the magnetic field to a user interface, which means has been arranged in connection with the sensor.

2. An imaging arrangement according to claim 1, wherein said means for producing a magnetic field is an inductive transmitter or a permanent magnet arranged in connection with the radiation source (4).

3. An imaging arrangement according to claim 1 wherein the means for measuring the strength of the magnetic field comprises at least one MRI detector (31) or such a coil (41, 32) in connection with which is arranged a means known as such for measuring the strength of the magnetic field from a signal to be received from the coil (41, 32).

4. An imaging arrangement according to claim 3, wherein there are three or four of said detectors (31) or coils (41, 32).

5. An imaging arrangement according to claim 4, wherein said detectors (31) or coils (41, 32) are arranged at the corners of an area forming at least an essentially equilateral triangle or a rectangle which essentially does not resemble a line.

6. An imaging arrangement according to claim 3, wherein at least one of said detectors (31) or coils (41, 32) is arranged to a different plane or angle on some surface relating to the sensor (30) or the radiation source (4), with respect to at least one other detector (31) or coil (41, 32).

7. An imaging arrangement according to claim 6, wherein said detectors (31) or coils (41, 32) are arranged perpendicularly with respect to one focus point.

8. An imaging arrangement according to claim 1, wherein said means for producing a magnetic field is an inductive transmitter arranged in connection with the radiation source (4) which transmitter is also arranged for supplying energy to the sensor (30) pertaining to the imaging arrangement.

9. An imaging arrangement according to claim 8, wherein said sensor (30) comprises a coil (32) of an inductive receiver essentially imitating the shape of the sensor housing perimeter.

10. An imaging arrangement according to claim 9, wherein a means known as such has been arranged in connection with the coil (32) of the inductive receiver for measuring the strength of the magnetic field from a signal received from the coil (41, 32).

11. An imaging arrangement according claim 1, wherein the user interface comprises a display device and wherein said user interface is a user interface of the control system of the imaging arrangement or that of another arrangement.

12. A method for positioning an X-ray source and a sensor with respect to each other in connection with intra-oral X-ray imaging, wherein at least one measurement signal is utilised in the positioning, which signal is received by arranging a means in connection with the radiation source for producing a magnetic field and a means in connection with the sensor for measuring the strength of the magnetic field, which measurement signal is then transmitted from the sensor to a user interface.

13. A method according to claim 12, wherein three or four measurement signals are utilized.

14. A method according to claim 13, wherein signals are measured from the corners of an area in the magnetic field of a shape of at least essentially an equilateral triangle or a rectangle not resembling a line.

15. A method according to claim 12, wherein the magnetic field is produced with an inductive transmitter arranged in connection with the radiation source (4).

* * * * *